(12) United States Patent
Park

(10) Patent No.: US 11,741,598 B2
(45) Date of Patent: Aug. 29, 2023

(54) METHOD FOR AIDING VISUALIZATION OF LESIONS IN MEDICAL IMAGERY AND APPARATUS USING THE SAME

(71) Applicant: VUNO, INC., Seoul (KR)

(72) Inventor: Gwangbeen Park, Seoul (KR)

(73) Assignee: VUNO, INC., Seoul (KR)

( * ) Notice: Subject to any disclaimer, the term of this patent is extended or adjusted under 35 U.S.C. 154(b) by 525 days.

(21) Appl. No.: 15/931,943

(22) Filed: May 14, 2020

(65) Prior Publication Data

US 2020/0364852 A1 Nov. 19, 2020

(30) Foreign Application Priority Data

May 14, 2019 (KR) ........................ 10-2019-0056142

(51) Int. Cl.
*G06T 7/00* (2017.01)
*G16H 30/20* (2018.01)
*G16H 50/30* (2018.01)

(52) U.S. Cl.
CPC ........... *G06T 7/0012* (2013.01); *G16H 30/20* (2018.01); *G16H 50/30* (2018.01); *G06T 2207/20084* (2013.01); *G06T 2207/20101* (2013.01); *G06T 2207/30096* (2013.01)

(58) Field of Classification Search
CPC ......... G06T 7/0012; G06T 2207/20084; G06T 2207/20101; G06T 2207/30096; G06T 2200/24; G06T 2207/10072; G06T 2207/20081; G06T 7/11; G06T 7/174; G06T 11/60; G06T 5/005; G06T 11/40; G06T 2210/41; G16H 30/20; G16H 50/30; G16H 50/20; G16H 30/40; G06F 3/0484
See application file for complete search history.

(56) References Cited

U.S. PATENT DOCUMENTS

| 9,772,390 B2 | 9/2017 | Park et al. |
| 9,996,918 B2 | 6/2018 | Kim et al. |
| 2014/0146076 A1* | 5/2014 | Kim ................. G06F 3/04845 345/619 |

FOREIGN PATENT DOCUMENTS

| JP | 2014-087635 A | 5/2014 |
| JP | 2014-106980 A | 6/2014 |
| JP | 2018-102916 A | 7/2018 |
| KR | 10-1611488 B1 | 4/2016 |
| KR | 10-2016-0118037 A | 10/2016 |

(Continued)

OTHER PUBLICATIONS

Kohl et al, A probabilistic u-net for segmentation of ambiguous images, Advances in Neural Information Processing Systems 31 (NeurIPS) (Year: 2018).*

(Continued)

*Primary Examiner* — Nay A Maung
*Assistant Examiner* — Xiao Liu
(74) *Attorney, Agent, or Firm* — IP & T Group LLP

(57) ABSTRACT

A computing apparatus for aiding visualization of lesions in a medical image includes a communicator and a processor. The processor is configured to receive a user input for selecting a single point in the medical image to modify a lesion mask representing a lesion area in them medical image, determine a modified lesion mask corresponding to the received user input among a plurality of pre-generated plurality of candidate lesion masks, and provide the modified lesion mask with the medical image.

9 Claims, 9 Drawing Sheets

(56) References Cited

FOREIGN PATENT DOCUMENTS

| KR | 10-1762678 B1 | 8/2017 |
| KR | 10-1874348 B1 | 7/2018 |
| KR | 10-1898575 B1 | 9/2018 |
| KR | 10-2019-0049524 A | 5/2019 |
| KR | 10-1953752 B1 | 6/2019 |

OTHER PUBLICATIONS

Khastavaneh et al, A Conceptual Model for Segmentation of Multiple Scleroses Lesions in Magnetic Resonance Images Using Massive Training Artificial Neural Network, 5th International Conference on Intelligent Systems, Modelling and Simulation, pp. 273-278 (Year: 2014).*

Park, G et al., Interactive Segmentation Mask Editing Tool with 3D Probabilistic Unet for Lung Nodule, MIDL 2019 Conference Abstract.

Office Action issued by the Japan Patent Office dated Nov. 10, 2020.

Kohl S.A.A. et al., A Probabilistic U-Net for Segmentation of Ambiguous Images, V4, 32nd Conference on Neural Information Processing Systems (NeurIPS 2018), Jan. 29, 2019, Montreal, Canada.

Kayahbay B et al., CNN-based Segmentation of Medical Imaging Data, V2, Jul. 25, 2011, ArXiv.

* cited by examiner

[FIG. 1A]
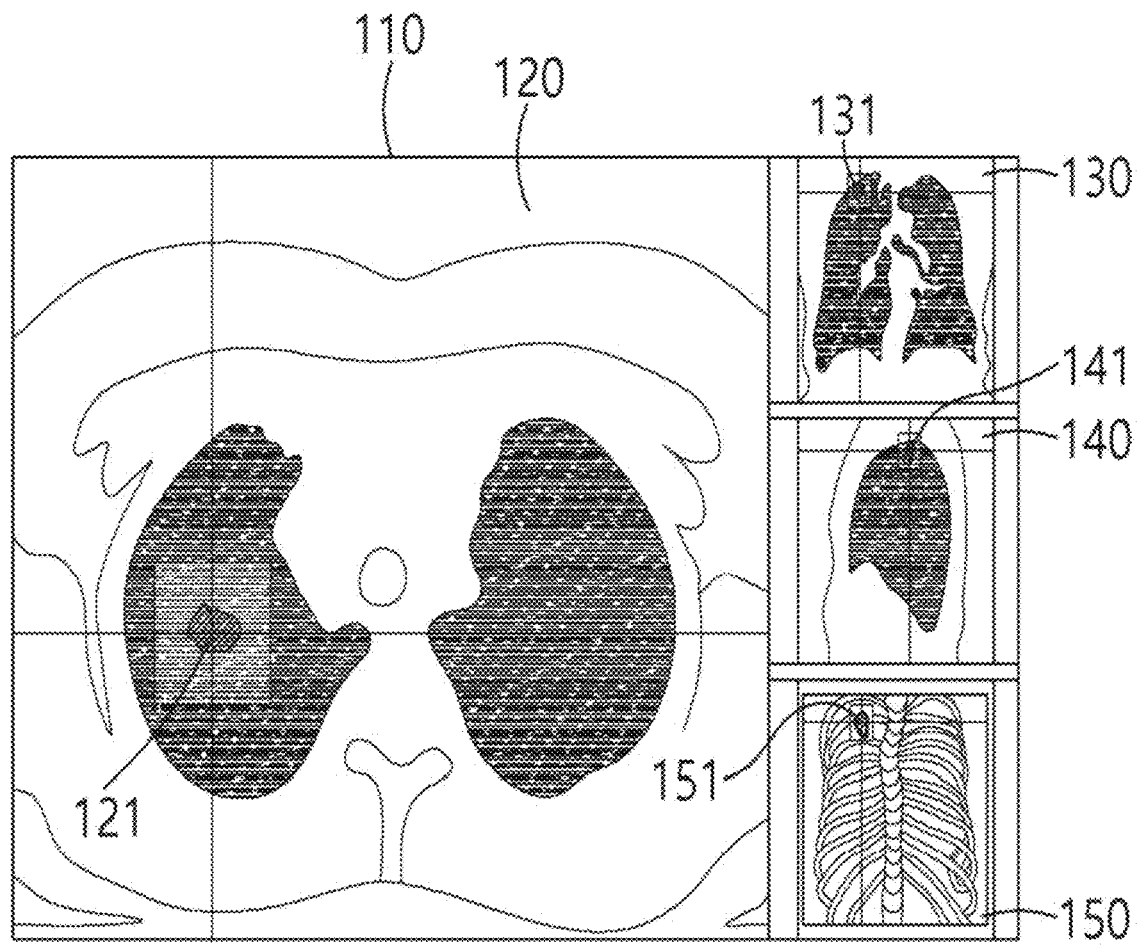

[FIG. 1B]
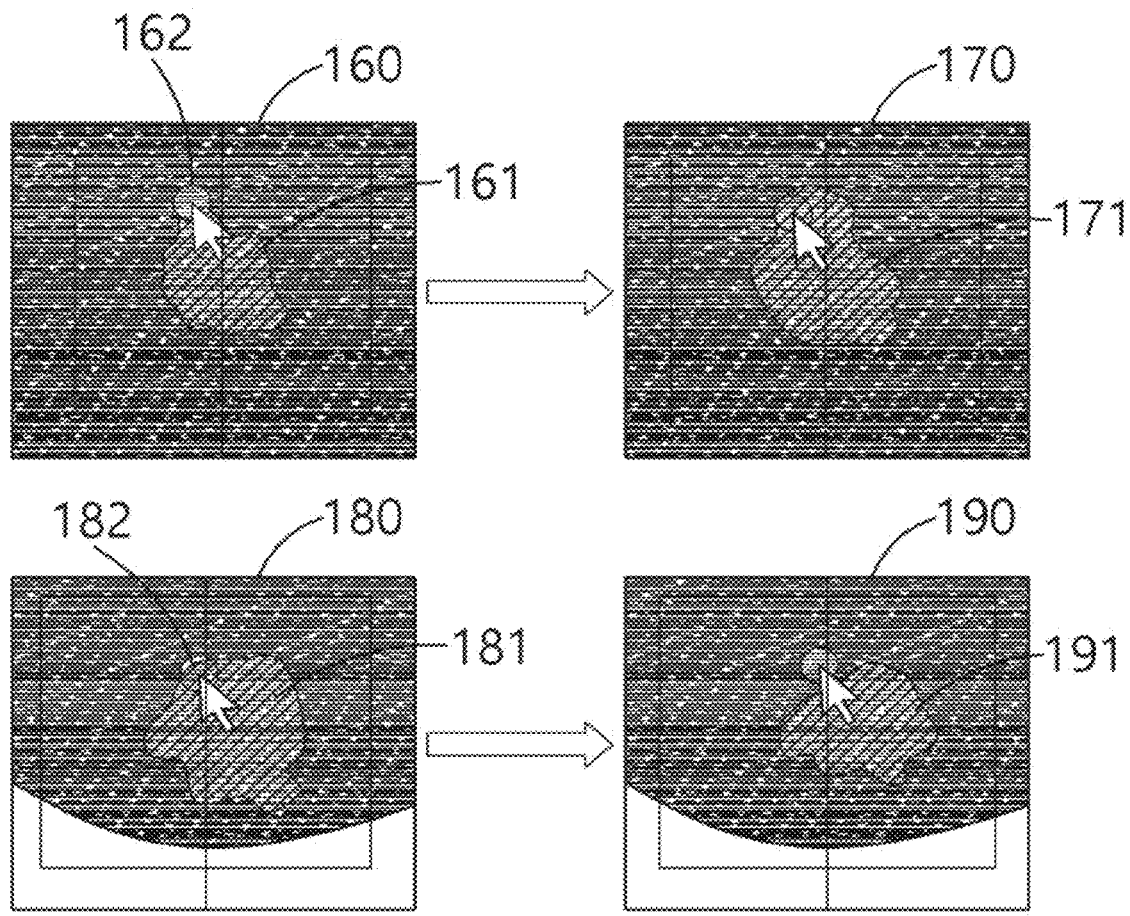

[FIG. 2]
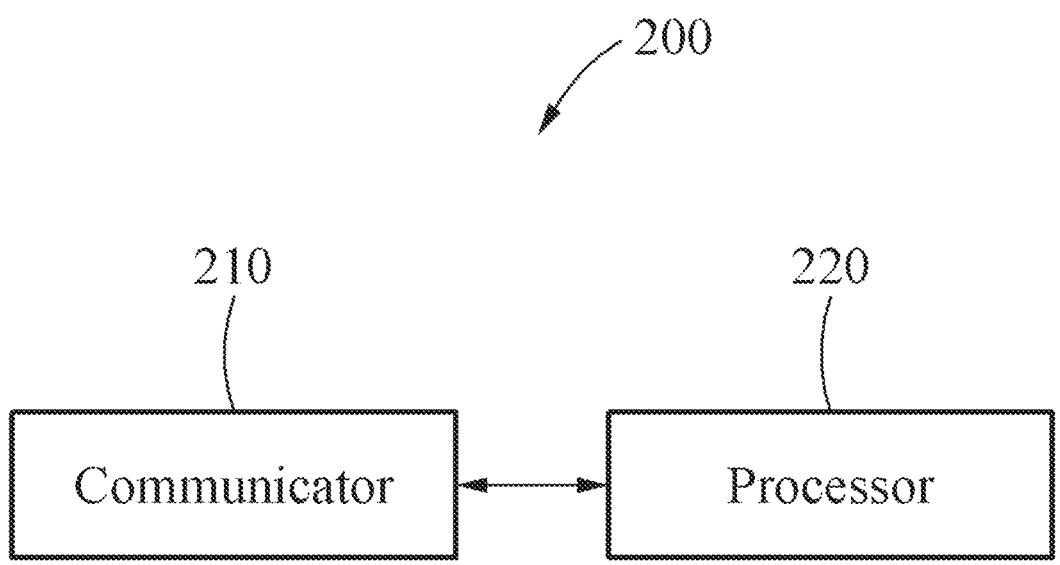

[FIG. 3]
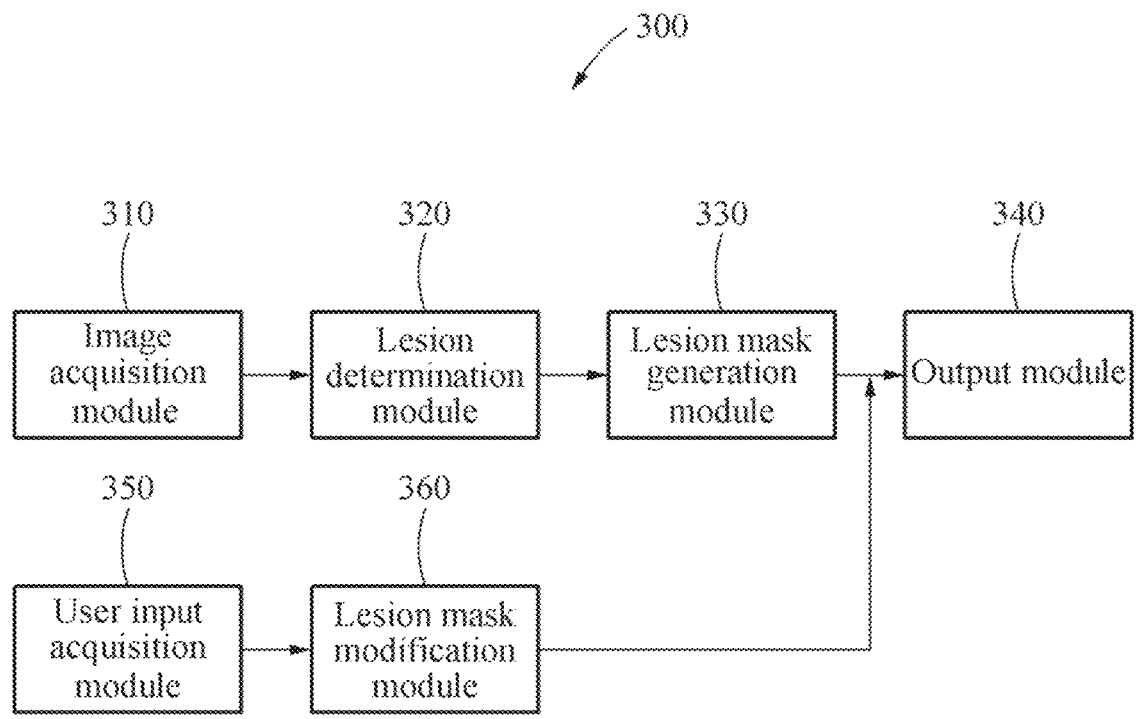

[FIG. 4]
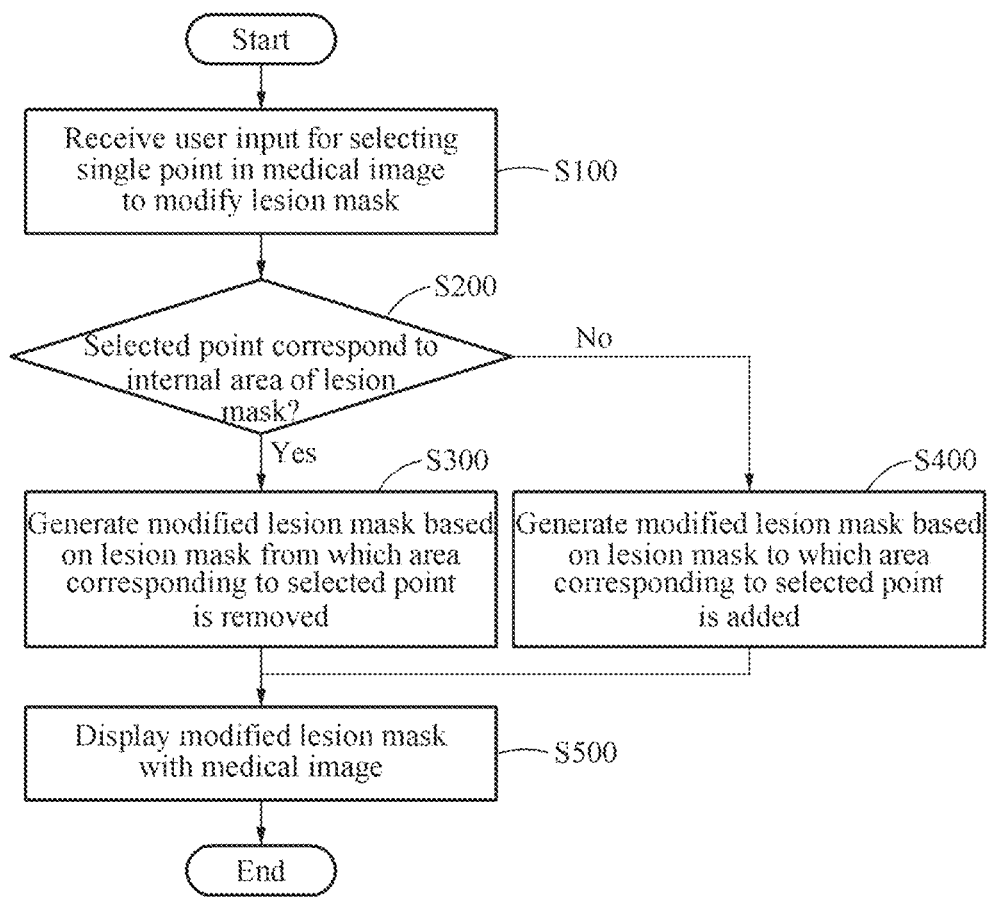

[FIG. 5]
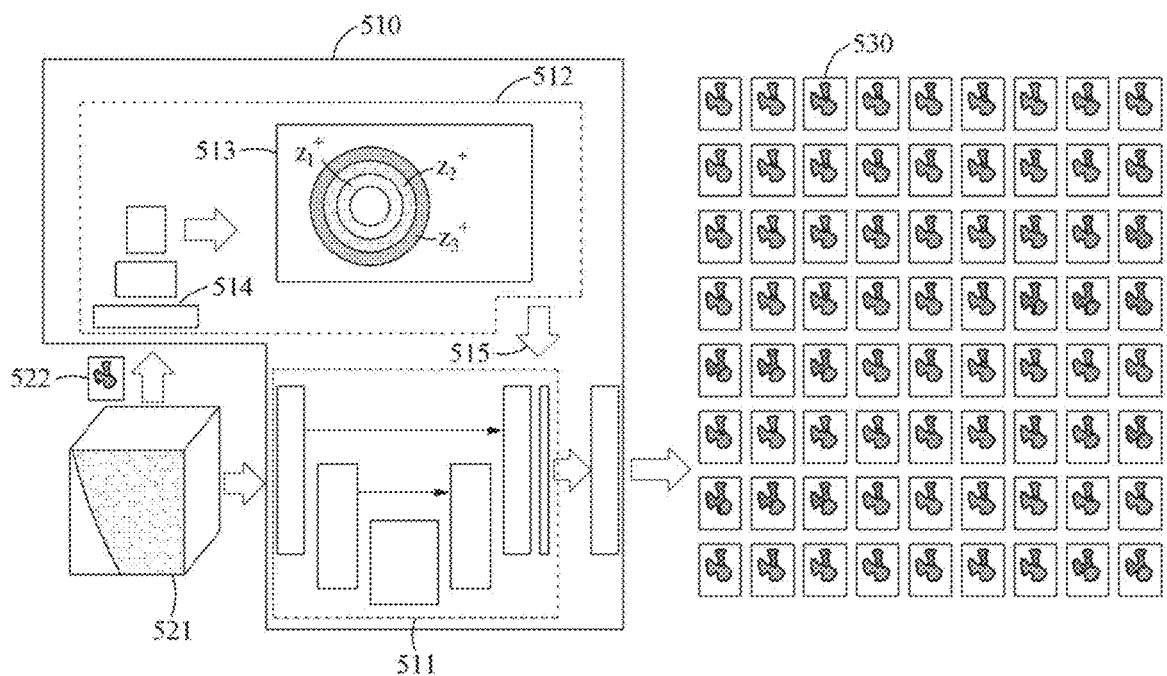

[FIG. 6A]
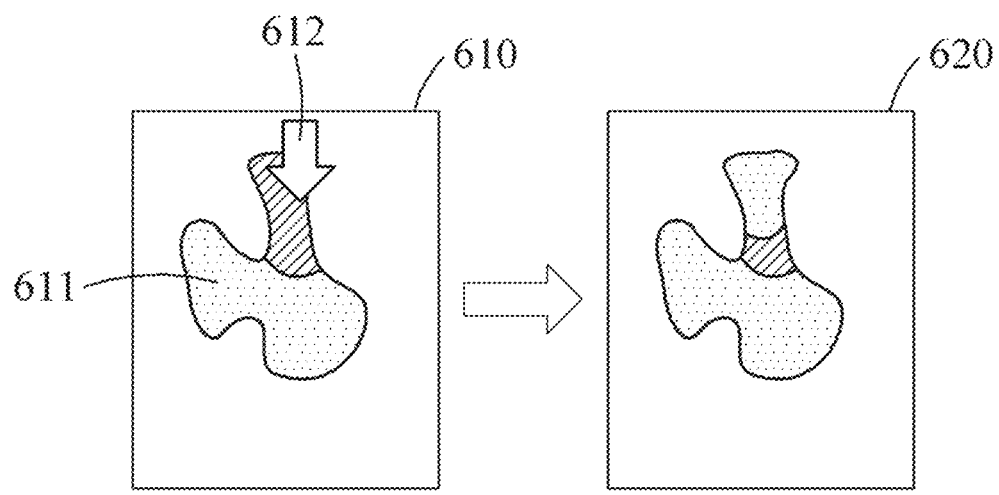

[FIG. 6B]
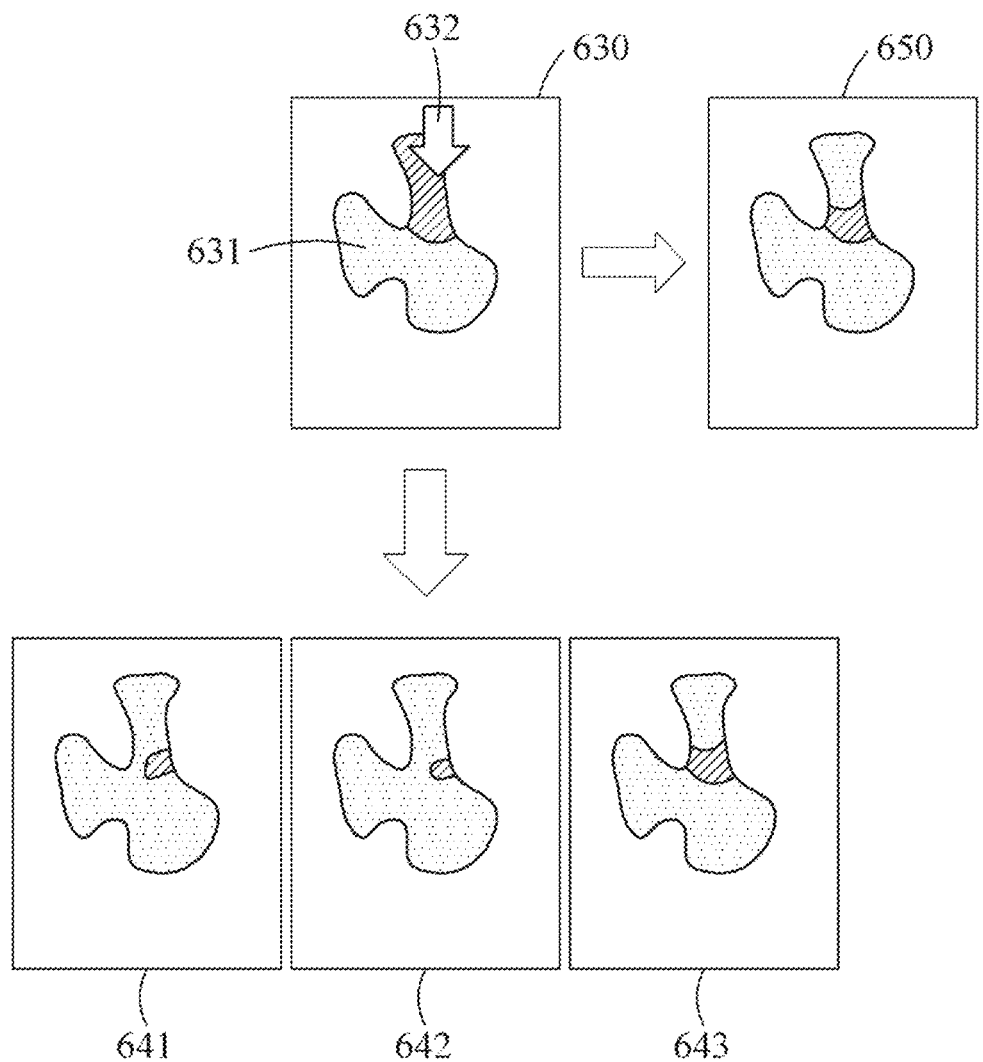

[FIG. 7]
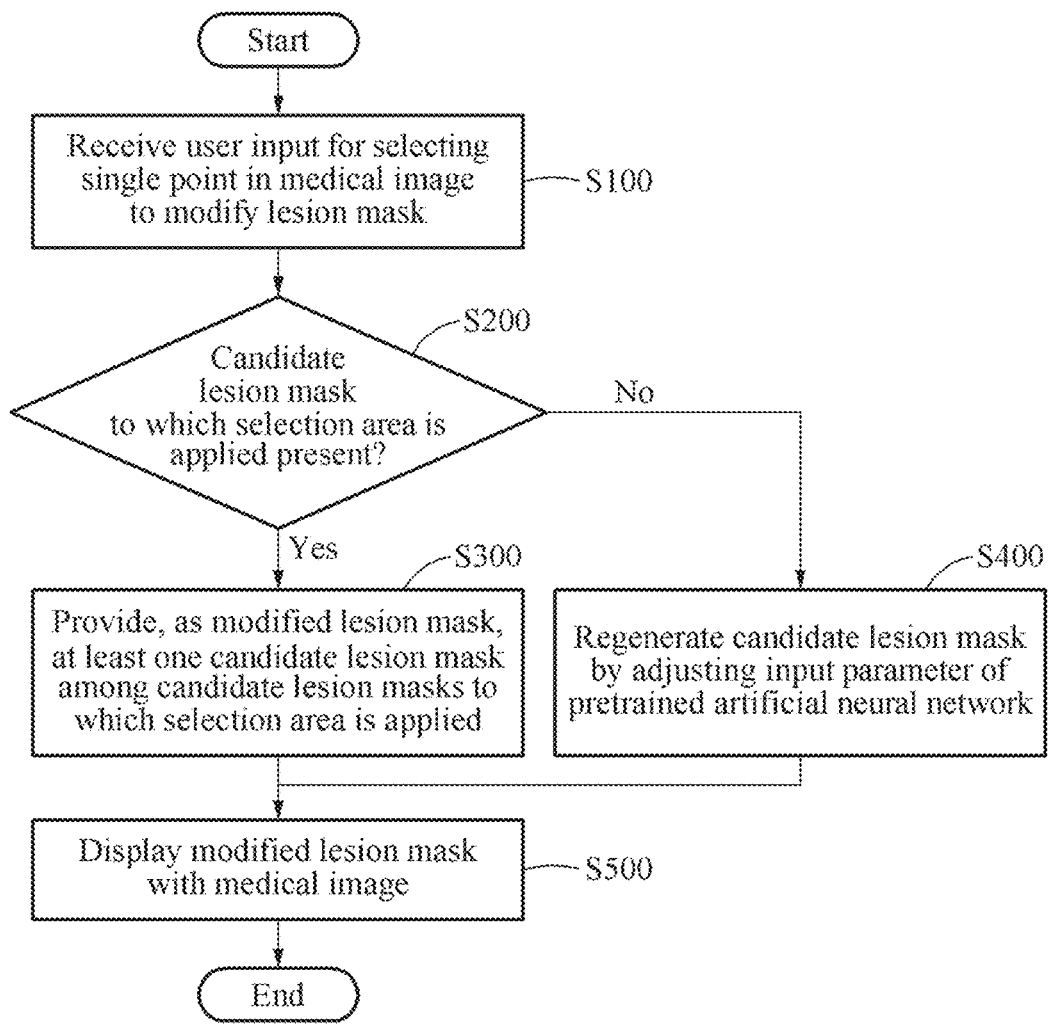

METHOD FOR AIDING VISUALIZATION OF LESIONS IN MEDICAL IMAGERY AND APPARATUS USING THE SAME

TECHNICAL FIELD

The present disclosure relates to a method of aiding visualization of lesions in a medical image and an apparatus using the same.

RELATED ART

A lesion mask represents a lesion area in a medical image and may be overlappingly displayed with the medical image. Since a lesion area may be differently judged even for the same medical image according to findings of a doctor, a method capable of modifying a lesion mask based on the judgment of the doctor is required. In an existing method of modifying a lesion mask, a user that reads a lesion in a medical image may modify a lesion mask by directly coloring an area determined as an additional lesion area using a mouse pointer that is provided as a "coloring tool." Also, the user may modify the lesion area through an operation of directly erasing, from a provided lesion mask, an area determined to be not a lesion area using a mouse pointer that is provided as an "erase tool."

Also, if a medical image corresponds to a three-dimensional (3D) image such as a computed tomography (CT) image, all of related tomographic images need to be modified to modify a lesion mask. Therefore, the existing method of directly coloring or erasing an area to be modified using a mouse pointer may have a degraded efficiency in terms of lesion mask modification.

Accordingly, proposed are herein a method capable of further easily modifying a lesion mask in a medical image and an apparatus using the same.

DETAILED DESCRIPTION

Technical Subject

The invention described herein, that is, the present invention is to provide an interface capable of easily modifying a lesion mask representing a lesion area in a medical image based on a single user input, such as a click.

In detail, in a lesion mask in which frequent modification occurs according to findings of a doctor, the present invention is to provide a method capable of efficiently performing modification compared to an existing method of modifying a lesion mask through an operation of coloring or removing an area of each lesion mask to be modified.

Solution

Characteristic constitutions of the present invention to accomplish the aforementioned objectives and to achieve characteristic effects of the present invention are as follows:

According to an aspect of the present invention, there is provided a method of aiding visualization of lesions in a medical image, the method including receiving a user input for selecting a single point in the medical image to modify a lesion mask representing a lesion area included in the medical image; generating a modified lesion mask in response to the user input; and providing the modified lesion mask with the medical image.

According to another aspect of the present invention, there is provided a computer program stored in a non-transitory computer-readable storage medium including instructions configured to cause a computing apparatus to perform the lesion visualization aiding method of the present invention.

According to still another aspect of the present invention, there is provided a computing apparatus for aiding visualization of lesions in a medical image, the computing apparatus including a communicator configured to detect, in a medical image combined with a lesion mask representing a lesion area, a user input for selecting a single point in the medical image to modify the lesion mask; and a processor configured to generate a modified lesion mask corresponding to the received user input. Here, the processor is configured to support an output device interacting through the communicator to provide the medical image combined with the modified lesion mask.

Effects

According to the present invention, it is possible modify a lesion mask through a simple user input, such as a single click. Through this, a reader may further efficiently modify a lesion mask compared to an existing method of modifying a lesion mask by directly coloring or deleting a desired area using a mouse point.

Therefore, according to the present invention, a speed and quality of readings may be improved in the field of reading in which a type of a lesion is differently judged according to a reader, which may lead to innovating the workflow in the medical field.

Further, the present invention may advantageously apply not only in the medical field of reading lesions in a medical image of an actual patient but also in a training process for improving an image reading ability, which may lead to improving the efficiency of a training process of a resident.

BRIEF DESCRIPTION OF DRAWINGS

Example embodiments will be described in more in detail with reference to the following figures that are simply a portion of the example embodiments and those skilled in the art to which the present invention pertains may readily acquire other figures based on the figures without an inventive work being made:

FIGS. 1A and 1B schematically illustrate a lesion visualization aiding method according to the present disclosure.

FIG. 2 is a diagram illustrating an example of a configuration of a computing apparatus configured to perform a lesion visualization aiding method according to the present disclosure.

FIG. 3 is a block diagram illustrating an example of hardware or software components of a computing apparatus configured to perform a lesion visualization aiding method according to the present disclosure.

FIG. 4 is a flowchart illustrating an example of a lesion visualization aiding method according to the present disclosure.

FIG. 5 illustrates an example of an artificial neural network used for a lesion visualization aiding method according to the present disclosure.

FIGS. 6A and 6B illustrate examples of applying a lesion visualization aiding method according to the present disclosure.

FIG. 7 is a flowchart illustrating an example of a lesion visualization aiding method according to another example embodiment.

BEST MODE

The following detailed description of the present invention is described with reference to the accompanying drawings in which specific example embodiments are illustrated as examples, to fully describe purposes, technical solutions, and advantages of the present invention. The example embodiments are described in detail enough for those skilled in the art to carry out the present invention.

Further, the term "image" or "image data" used throughout the detailed description and the claims herein refers to multi-dimensional data that includes discrete image factors (e.g., pixels in a two-dimensional (2D) image and voxels in a three-dimensional (3D) image).

For example, the term "image" may refer to a medical image of a subject collected by cone-beam computed tomography (CT), magnetic resonance imaging (MRI), an ultrasound system, or other medical image systems known in the field to which the present invention pertains. Also, the image may be provided in a non-medical context, for example, a remote sensing system, an electron microscopy, and the like.

The term "image" used throughout the detailed description and the claims of this disclosure may refer to an image that is visible with an eye (e.g., displayed on a video screen) or a digital representation of an image (e.g., a file corresponding to a pixel output of CT, an MRI detector, and the like).

For clarity of description, cone-beam computed tomography (CBCT) image data is illustrated in the drawings as an exemplary image modality. However, it will be apparent to those skilled in the art that image modalities used in various example embodiments of the present invention may include X-ray images, MRI, CT, positron emission tomography (PET), PET-CT, single photo emission computed tomography (SPECT), SPECT-CT, MR-PET, 3D ultrasound images, and the like, without being limited thereto.

The term "Digital Imaging and Communications in Medicine (DICOM)" standard used throughout the detailed description and the claims of this disclosure is a generic term for a plurality of standards used for digital image representation and communication in medical devices. The DICOM standard is published by the American College of Radiology (ACR) and the National Electrical Manufacturers Association (NEMA).

Also, the term "Picture Archiving and Communication System (PACS)" used throughout the detailed description and the claims of this disclosure is a term for systems that perform storage, processing, and transmission according to the DICOM standard. A medical image acquired using digital medical imaging equipment, such as X-ray, CT, and MRI, may be stored in a DICOM format and may be transmitted to a terminal inside or outside a hospital over a network. Here, a reading result and a medical record may be added to the medical image.

Further, the term "training" or "learning" used throughout the detailed description and the claims of this disclosure refers to performing a machine learning through computing according to a procedure and it will be apparent to those skilled in the art that the term is not intended to refer to a mental action such as an educational activity of a human.

Also, the terms "comprises/includes" used throughout the detailed description and the claims of this disclosure are not intended to exclude other technical features, additions, components, or operations. Also, "single" or "one" is used to indicate at least one and "another" is limited to at least second or more.

Those skilled in the art may clearly understand a portion of other purposes, advantages, and features of the disclosure from this specification and another portion thereof from implementations of the disclosure. The following examples and drawings are provided as examples only and not to limit the disclosure. Therefore, the detailed description disclosed herein should not be interpreted as a limiting meaning with respect to a specific structure or function and should be interpreted as representative basic data that provides guidelines such that those skilled in the art may variously implement the disclosure as substantially suitable detailed structures.

Further, the present invention may include any possible combinations of example embodiments described herein. It should be understood that, although various example embodiments differ from each other, they do not need to be exclusive. For example, a specific shape, structure, and feature described herein may be implemented as another example embodiment without departing from the spirit and scope of the disclosure. Also, it should be understood that a position or an arrangement of an individual component of each disclosed example embodiment may be modified without departing from the spirit and scope of the disclosure. Accordingly, the following detailed description is not to be construed as being limiting and the scope of the disclosure, if properly described, is limited by the claims, their equivalents, and all variations within the scope of the claims. In the drawings, like reference numerals refer to like elements throughout.

Unless the context clearly indicates otherwise, the singular forms "a," "an," and "the," are intended to include the plural forms as well. Also, when description related to a known configuration or function is deemed to render the present disclosure ambiguous, the corresponding description is omitted.

Hereinafter, example embodiments of the disclosure are described in detail with reference to the accompanying drawings such that those skilled in the art may easily perform the example embodiments.

FIGS. 1A and 1B schematically illustrate a lesion visualization aiding method according to the present disclosure.

FIG. 1A illustrates an example of an interface 110 for providing a lung image in which lesion masks representing lesion areas are overlapped. The interface 110 provides a medical image captured at a variety of viewpoints through sub-screens 120, 130, 140, and 150. Lesion areas may be visualized in the medical image provided through corresponding lesion masks 121, 131, 141, and 151 provided through the respective sub-screens 120, 130, 140, and 150. A reader that reads the medical image may observe lesion areas at various angles through the sub-screens 120, 130, 140, and 150 and accordingly, may further accurately read a diameter and volume of a lesion.

A lesion visualization aiding method according to an example embodiment may provide an interface capable of further easily modifying a lesion mask through a single user input, such as a touch.

In detail, referring to FIG. 1B, in response to receiving a user input 162 for adding a single area to a lesion mask 161 in a medical image 160 to which the lesion mask 161 is applied, an image lesion visualization aiding apparatus may generate a lesion mask 171 in which a single area selected by the user input 162 is added to the lesion mask 161 and may provide a medical image 170 overlapped with the generated lesion mask 171.

Also, in response to receiving a user input 182 for removing a single area from a lesion mask 181 in a medical image 180 to which the lesion mask 181 is applied, the image lesion visualization aiding apparatus may provide a medical image 190 overlapped with a lesion mask 191 from which an area selected by the user input 182 is removed.

The lesion visualization aiding method of the present invention may provide a method capable of efficiently modifying a lesion mask through a simple user input, such as a touch, compared to an existing method that requires a user input for directly coloring or removing all of areas to be modified during a lesion mask modification process.

FIG. 2 is a diagram illustrating an example of a configuration of a computing apparatus configured to perform a method of aiding visualization of lesions according to the present disclosure.

Referring to FIG. 2, a computing apparatus 200 according to an example embodiment of the present disclosure includes a communicator 210 and a processor 220, and may directly or indirectly communicate with an external computing apparatus (not shown) through the communicator 210.

In detail, the computing apparatus 200 may achieve a desired system performance using a combination of typical computer hardware (e.g., an apparatus including a computer processor, a memory, a storage, an input device and an output device, components of other existing computing apparatuses, etc.; an electronic communication apparatus such as a router, a switch, etc.; an electronic information storage system such as a network-attached storage (NAS) and a storage area network (SAN)) and computer software (i.e., instructions that enable a computing apparatus to function in a specific manner).

The communicator 210 of the computing apparatus may transmit and receive a request and a response with another interacting computing apparatus. As an example, the request and the response may be implemented using the same transmission control protocol (TCP) session. However, it is provided as an example only. For example, the request and the response may be transmitted and received as a user datagram protocol (UDP) datagram. In addition, in a broad sense, the communicator 210 may include a keyboard, a mouse, and other external input devices to receive a command or an instruction, etc., and a printer, a display, and other external input devices.

Also, the processor 220 of the computing apparatus may include a hardware configuration, such as a micro processing unit (MPU), a central processing unit (CPU), a graphics processing unit (GPU), a tensor processing unit (TPIJ), a cache memory, a data bus, and the like. Also, the processor 120 may further include a software configuration of an application that performs a specific objective, an operating system (OS), and the like.

FIG. 3 is a diagram illustrating an example of hardware or software components of a computing apparatus configured to perform a lesion visualization aiding method according to the present disclosure.

Describing a method and a configuration of an apparatus according to the present disclosure with reference to FIG. 3, the computing apparatus may include an image acquisition module 310 as a component. The image acquisition module 310 is configured to acquire a medical image to which the method according to the present disclosure applies. It will be apparent to those skilled in the art that individual modules of FIG. 3 may be configured through, for example, the communicator 210 or the processor 220 included in the computing apparatus 200, or through interaction between the communicator 210 and the processor 220. The medical image may be acquired from an external image storage system, such as, for example, a photographing device interacting through the communicator 210 or Picture Archiving and Communication System (PACS). However, it is provided as an example only. For example, a medical image may be captured by a (medical) imaging device and transmitted to the PACS according to the DICOM standard and then, acquired by the image acquisition module 310 of the computing apparatus.

The acquired medical image may be forwarded to a lesion determination module 320. The lesion determination module 320 is configured to determine a suspected lesion area that is an area suspected as a lesion in the medical image. The lesion determination module 320 may be a lesion determination model configured to determine whether each pixel of the medical image corresponds to a lesion area or a module associated therewith.

An example of the lesion determination module or the lesion determination model 320 may include a deep learning model, which is in a structure in which an artificial neural network is stacked in multiple layers. That is, it may be represented as a deep neural network as a meaning of a deep structured network. The network may be trained by learning a large amount of data in a multilayered network structure and thereby automatically learning features of each image and accordingly, minimizing an error of an objective function. It is compared to connectivity between neural cells of the human brain. Such a deep neural network is becoming a next generation model of artificial intelligence (AI). In particular, among examples of the deep learning model, a convolutional neural network (CNN) may be a model suitable for classifying images and may extract various levels of features ranging from a low level feature, such as a dot, a line, a surface, etc., to a high level feature, which is complex and significant, by repeating a convolution layer for generating a feature map of each area using a plurality of filters and a sub-sampling layer for extracting an invariant feature against a change in a position or a rotation through a reduction in a size of the feature map. Through this, suspected lesions that are portions having specific features may be extracted from the medical image.

However, it will be understood by those skilled in the art that the lesion determination module or the lesion determination model is not limited to the CNN. Accordingly, various types of machine learning models or statistical models may be used. In detail, the lesion determination module 320 may determine a lesion through one of a rule-based neural network, a learning-based neural network, and a method that allows a user to directly label a lesion area.

A lesion mask generation module 330 may generate a lesion mask corresponding to the lesion area based on a lesion determination result by the lesion determination module 320. The lesion mask may be a factor that enables a reader to easily identify the lesion area by representing the lesion area included in the medical image as a factor distinguished from the medical image. For example, as shown in FIG. 1, the lesion mask may be represented by representing a predetermined lesion area using a predetermined color. However, it is provided as an example only and a type of the lesion mask is not limited thereto. The lesion mask may be generated using any arbitrary method capable of distinguishing the medical image and the lesion area from each other.

The lesion mask generation module 330 may generate a plurality of candidate lesion masks corresponding to the lesion determination result based on the pretrained artificial neural network. The pretrained artificial neural network may be trained to generate a plurality of lesion masks in response to an input of the medical image (or a patch for the medical image and the lesion area in the medical image). For example, the pretrained artificial neural network may be generated based on a combination of a conditional variational auto encoder (CVAE) and U-Net used for medical image segmentation.

Each of the plurality of candidate lesion masks may have a different shape. That is, each of lesion areas identified through the plurality of candidate lesion masks may differ for each candidate lesion mask. The pretrained artificial neural network may be in the same structure as that of a neural network of FIG. 5.

The pretrained artificial neural network may adjust a number of candidate lesion masks to be generated by adjusting a parameter. For example, the pretrained artificial neural network may generate a predetermined number of candidate lesion masks, such as 16, 64, 128, etc., candidate lesion masks, based on a parameter. Those skilled in the art may understand that higher load may apply to a system as a larger number of lesion masks are generated.

An output module 340 may overlap the lesion mask on the medical image and thereby provide, for example, display the same through a predetermined output device to be connected through the communicator 210.

The lesion mask provided through the output module 340 may be modified according to findings of a reader. The reader may exclude a partial area of the lesion mask from the lesion mask or may add an adjacent area to the lesion mask through a single click or touch on the medical image or a lesion mask area that is overlapping provided with the medical image.

A user input acquisition module 350 may receive a user input for modifying a lesion mask through the communicator 210 and, in response to the received user input, a lesion mask modification module 360 may modify the lesion mask generated by the lesion mask generation module 330.

The output module 340 may overlappingly output the medical image and the lesion mask modified through the lesion mask modification module 360 to an external entity through an output device connected through the communicator 210.

Here, the external entity may include a user of the computing apparatus, a manager, a medical expert in charge of the subject, and, in addition thereto, may also include any types of entities that require viewing or reading of the medical image.

Functions and effects of components shown in FIG. 3 are further described below. Although the components of FIG. 3 are illustrated in a single computing apparatus for clarity of description, the computing apparatus that performs the method of the present invention may be configured such that a plurality of apparatuses may interact with each other.

Hereinafter, an example embodiment of the lesion visualization aiding method according to the present disclosure is further described with reference to FIGS. 4 to 6.

FIG. 4 is a flowchart illustrating an example of a lesion visualization aiding method according to the present disclosure. FIG. 4 schematically illustrates an example embodiment of the lesion visualization aiding method according to the present disclosure.

Referring to FIG. 4, overall, in the lesion visualization aiding method according to the present disclosure, if a user input for modifying a lesion mask provided through the lesion mask generation module 330 is detected in operation S100, a computing apparatus may determine whether a point at which the detected user input is performed corresponds to an existing lesion mask area using the lesion mask modification module 360.

If the point at which the user input is performed corresponds to an internal area of the lesion mask in operation S200, the lesion mask modification module 360 may generate a modified lesion mask based on a lesion mask from which a selection area determined based on the user input is excluded in operation S300. For example, the selection area may be determined as an area corresponding to a radius preset based on the point at which the user input is performed. However, it is provided as an example only. A method of determining a selection area based on a user input may include any methods of determining the selection area based on a point at which the user input is performed. According to an example embodiment, the lesion mask modification module 360 may generate a modified lesion mask based on a lesion mask from which the selection area is excluded, among a plurality of lesion masks generated by inputting information about an existing lesion mask and the selection area to the pretrained artificial neural network. In detail, the lesion mask modification module 360 may generate a modified lesion mask based on a lesion mask including an area of a lesion mask before modification and not including the selection area determined based on the user input, among a plurality of lesion masks generated by inputting information about an existing lesion mask and information about a 3D patch corresponding to the selection area to the pretrained artificial neural network. In operation S500, the computing apparatus may provide, for example, display the medical image overlapped with the modified lesion mask to the external entity through the output module 340.

According to still another example embodiment, the lesion mask modification module 360 may provide a user with a plurality of candidate lesion masks from which a selection area is excluded, among a plurality of lesion masks generated by inputting information about an existing lesion mask and information about the selection area to the pretrained artificial neural network, and may determine, as a final lesion mask, a single candidate lesion mask selected based on the user input. For example, the lesion mask modification module 360 may determine selection areas based on different radiuses based on a point at which the user input is performed, and may determine, as candidate lesion masks, lesion masks from which the respective selection areas are excluded. A method of selecting a candidate lesion mask is not limited to the aforementioned example and may include any methods of determining a plurality of candidate lesion masks from which selection areas according to a user input are excluded among lesion masks generated through the artificial neural network.

If the point at which the user input is performed corresponds to an external area of the lesion mask in operation S200, the lesion mask modification module 360 may generate a modified lesion mask based on a lesion mask further including the selection area determined based on the user input in operation S400.

According to an example embodiment, the lesion mask modification module 360 may generate a modified lesion mask based on a lesion mask that includes a selection area among a plurality of lesion masks generated by inputting information about an existing lesion mask and information about the selection area to the pretrained artificial neural network. In detail, the lesion mask modification module 360 may generate a modified lesion mask based on a lesion mask including an area of a lesion mask before modification and a selection area among a plurality of lesion masks generated by inputting, to the pretrained artificial neural network, information about a medical image to which an existing lesion mask is applied and information about the selection area. In operation S500, the computing apparatus may provide the external entity with the medical image overlapped with the modified lesion mask through the output module 340.

According to still another example embodiment, the lesion mask modification module 360 may provide the user with a plurality of candidate lesion masks including an area of a lesion mask before modification and a selection area among a plurality of lesion masks generated by inputting, to the pretrained artificial neural network, information about a medical image to which an existing lesion mask is applied and information about the selection area, and may determine, as a final lesion mask, a single candidate lesion mask selected based on the user input.

FIG. 5 illustrates an example of an artificial neural network used for a lesion visualization aiding method according to the present disclosure.

An artificial neural network 510 of FIG. 5 may output a plurality of lesion masks 530 based on a 3D patch 521 corresponding to a selection area that is determined based on a user input, and information about an existing lesion mask 522.

The artificial neural network 510 may be generated based on combination of a conditional variation auto encoder (CVAE) 512 and U-Net 511 used for medical image segmentation. The CVAE 512 may include a map 513 in which a segmentation variant is encoded at each location and a network 514 configured to estimate a probability of each segmentation variant based on an input.

In a process of generating each lesion mask 530, the CVAE 512 of the artificial neural network 510 may extract a single encoded sample ($Z_1, Z_2, Z_3 \ldots$) from the map 513, and the artificial neural network 510 may generate the lesion mask 530 based on the extracted sample and output from the U-Net 511.

The artificial neural network 510 may be trained by determining optimal embedding about a segmentation variant based on ground truth data and a lesion mask predicted through training data.

FIGS. 6A and 6B illustrate examples of applying a lesion visualization aiding method according to the present disclosure. Referring to FIG. 6A, a reader may perform a user input 612 for including a predetermined area in a lesion mask in a medical image 610 overlapped with a lesion mask 611. In response to detecting the user input 612, a computing apparatus may display a medical image 620 overlapped with a lesion mask that is determined to most excellently represent the intent of the reader based on a predetermined condition among a plurality of lesion masks generated through the lesion mask 611 and the user input 612 using a pretrained artificial neural network. The lesion mask that most excellently represents the intent of the reader may correspond to a lesion mask that all of selection areas determined based on the user input 612 are added or excluded. If the displayed medical image 620 does not meet the intent, the reader may proceed with an addition user input for modifying the medical image 620 and the computing apparatus may provide a modified lesion mask based on the additional user input and the lesion mask. Modification of the lesion mask may be repeated until the reader does not perform an additional modification request.

FIG. 6B illustrates an example of applying a lesion visualization aiding method according to another example embodiment. When the reader performs a user input 632 for modifying a lesion mask 631 of a provided medical image 630, the computing apparatus detecting the user input 632 may generate a plurality of lesion masks to which the user input 632 is applied using a pretrained artificial neural network and may provide a predetermined number of candidate lesion masks 641, 642, and 643 that most excellently represent the intent of the reader among the generated lesion masks. The computing apparatus may display a medical image 650 overlapped with the lesion mask 641 selected by the reader from among the candidate lesion masks 641, 642, and 643.

Although FIGS. 6A and 6B illustrate that areas of medical images corresponding to the lesion masks 611 and 631 are not displayed due to the lesion masks 611 and 631 in an opaque form, the example embodiments of the present disclosure are not limited thereto. As shown in FIGS. 1A and 1B, the lesion masks 611 and 631 may have a certain degree of transparency to reflect the medical images.

FIG. 7 is a flowchart illustrating a lesion visualization aiding method according to another example embodiment.

Referring to FIG. 7, in the lesion visualization aiding method, a computing apparatus may receive a user input for selecting a single point in a medical image to modify a lesion mask in operation S100.

In operation S200, the computing apparatus may determine whether a candidate lesion mask in which modification based on a selection area is applied to a provided lesion mask is present among a plurality of candidate lesion masks generated using a pretrained artificial neural network. For example, the candidate lesion mask in which modification based on the selection area is applied to the provided lesion mask may refer to i) a candidate lesion mask corresponding to a form that includes all of the provided lesion mask and the selection area if the user input is performed on an external area of the provided lesion mask among areas of the medical image, or ii) a candidate lesion mask corresponding to a form in which the selection area is excluded from the provided lesion mask if the user input is performed on an internal area of the provided lesion mask among the areas of the medical image.

The computing apparatus may determine, as the modified lesion mask, a candidate lesion mask to which the selection area is applied by a preset threshold or more among the plurality of candidate lesion masks pre-generated using the pretrained artificial neural network. Here, since at least one lesion mask is selected from among the pre-generated candidate lesion masks, a lesion mask to which the selection area is fully applied may be absent. Depending on example embodiments, a lesion mask in which an area aside from the selection area is additionally modified may be provided. Therefore, the modified lesion mask may be determined based on a method of selecting a lesion mask that includes at least a predetermined ratio of the aforementioned selection area.

The pretrained artificial neural network may be an artificial neural network pretrained to generate a plurality of candidate lesion masks corresponding to a lesion area detected from the input medical image. Additionally, the pretrained artificial neural network may generate a plurality of candidate lesion masks corresponding to a parameter by using the parameter for determining a number of lesion masks to be generated as an input in addition to the input medical image. Depending on example embodiments, the pretrained artificial neural network may be an artificial neural network i) trained to generate a plurality of candidate lesion masks by using the medical image as an input, ii)

trained to generate the plurality of candidate lesion masks by using information about a lesion area of the medical image and the medical image, or iii) trained to generate the plurality of candidate lesion masks by using a parameter about a number of candidate lesion masks generated through i), ii) as an additional input.

If a candidate lesion mask corresponding to a lesion mask in which modification according to the selection area is applied to the provided lesion mask is determined to be present in operation S200, the computing apparatus may provide the corresponding candidate lesion mask as a modified lesion mask in operation S300. Depending on example embodiments, if a plurality of candidate lesion masks corresponding to the lesion mask to which the modification is applied is present, the computing apparatus may i) provide all of the plurality of candidate lesion masks and may determine, as a final modified lesion mask, a candidate lesion mask that is additionally determined based on a user input, or ii) determine, as the final modified lesion mask, a candidate lesion mask in which the selection area is applied to the provided lesion mask by a highest ratio.

Depending on example embodiments, the selection area may be a point area corresponding to a location of a single point at which the user input is performed or an area corresponding to straight line that connects two different points determined based on the user input. For example, the selection area corresponding to the straight line may be automatically generated based on user inputs selecting two different points or may be determined based on a user input corresponding to a drag by selecting and dragging a single point. In addition, the selection area may be determined as a circular shape having a predetermined radius based on a single point at which the user input is performed. A size or a shape of the selection area may be adjusted. For example, a radius of a circle may be adjusted and a shape of the circle may be adjusted to be an oval shape.

Also, the selection area may be an area in a 3D form. For example, the selection area may be determined as a spherical area using, as a center, a single point at which the user input is performed. In another example, the selection area may be determined as an arbitrary 3D form area created based on a 2D form area which is created based on a single point at which user input was performed, and an adjustable depth information.

In addition, the selection area may be determined based on pixel information of a single point at which the user input is performed. For example, if a user input for adding a predetermined area to a lesion mask area is performed at a single point in the medical image, areas corresponding to pixels having a predetermined degree of similarity to a pixel of the single pixel may be determined as the selection area.

Additionally, the user input may include an additional user input for further effectively determining a modified lesion mask. According to an example embodiment, the user input may include a first user input for determining a first selection area that is an area to be modified and a second user input for determining a second selection area that is an area to be non-modified, during a modification process of a provided lesion mask. As a result, a final modified lesion mask may be determined as a candidate lesion mask corresponding to a form in which the first selection area is modified and the second selection area is not modified in an existing lesion mask. The user may determine the final modified lesion mask by repeatedly performing modification based on the first user input for adding or removing a predetermined area. During this process, the final modified lesion mask may be further effectively generated based on the second user input for identifying a partial area (an area that is to be maintained during the modification process corresponding to the intent of the user in the modified entire area in previous modification process. For example, in a first modified lesion mask to which a predetermined area is added through a primary modification, a second area in the added area may apply the intent of the user and a first area may be represented to be different from the intent of the user. In this case, a lesion mask to which an additional modification is applied may be selected from among a plurality of candidate lesion masks pre-generated through an additional user input for the first area and the selected lesion mask may be provided. number of candidate lesion masks pre-generated through the artificial neural network is limited. Therefore, a lesion mask in which a portion of the second area is remodified may be provided during a process of repeating a modification. The present invention may improve the efficiency in modifying a lesion mask through the second user input distinguished from the first user input. In detail, the computing apparatus may provide a method capable of further quickly determining a remodified lesion mask through low load by determining a remodified lesion mask (to which the first selection area is applied) in a candidate lesion mask in which an area identified by the second user input is not modified among the pre-generated plurality of candidate lesion masks. Also, the computing apparatus may determine a method capable of further accurately and quickly determining a lesion mask to which the intent of the user is applied.

The computing apparatus may determine a modified lesion mask based on pixel information of a selected area or pattern information of the selected area as well as information about a shape of an area in which the user input is performed. For example, the computing apparatus may provide, as a modified lesion mask, a candidate lesion mask in which an area having a high similarity to a pixel value of the selection area or a pattern of pixels included in the selection area is added or removed from an existing lesion mask over the overall medical image (e.g., the entire slice image included in a 3D medical image). Through this, compared to a method of providing a lesion mask to/from which a preset form is added or removed based on the selection area, it is possible to provide a modified lesion mask to which the intent of the user is further effectively applied.

If the lesion mask to which the selection area is applied is determined to be absent in operation S200, the computing apparatus may regenerate a candidate lesion mask by adjusting an input parameter of the pretrained artificial neural network in operation S400. For example, if the selection area is applied in the provided lesion mask by less than a preset threshold, the computing apparatus may determine that the lesion mask to which the selection area is applied is absent.

If the lesion mask to which the selection area is applied is absent, the computing apparatus may adjust the input parameter such that the artificial neural network may generate a greater number of candidate lesion masks. A greater number of candidate lesion masks in various forms may be generated based on the adjusted input parameter. In this case, a probability that a candidate lesion mask reflecting the selection area may be generated may increase. As described above, by gradually increasing a parameter about a number of candidate lesion masks to be generated, the computing apparatus may provide a method of efficiently providing the modified lesion mask and, at the same time, saving computing load.

Depending on example embodiments, when candidate lesion masks in further various forms are generated through operation S400, the computing apparatus may additionally perform an operation of applying the aforementioned second selection area to the regenerated candidate lesion mask. Based on the aforementioned operation, the second selection area may be an area to which the intent of the user is applied. The modified lesion mask to which the intent of the user is applied may be further effectively generated by integrally applying the second selection area to the regenerated candidate lesion mask.

Also, if the lesion mask to which the modification corresponding to the selection area is applied is determined to be absent in operation S200, the computing apparatus may provide a method capable of directly modifying the lesion mask through the user input. For example, if a size of the selection area determined through the user input is less than or equal to a preset threshold, the computing apparatus may provide a method that allows the user to directly modify the lesion mask. Also, if the size of the selection area is greater than the preset threshold, the computing apparatus may perform operation S400. Through this, the computing apparatus may provide a method of saving computing load by providing a different modification scheme based on a degree by which a selection point is not applied.

In operation S500, the computing apparatus may provide, for example, display the medical image overlapped with the modified lesion mask to the external entity.

One of ordinary skill in the art may easily understand that the methods and/or processes and operations described herein may be implemented using hardware components, software components, or a combination thereof based on the example embodiments. For example, the hardware components may include a general-purpose computer and/or exclusive computing apparatus or a specific computing apparatus or a special feature or component of the specific computing apparatus. The processes may be implemented using at least one microprocessor having an internal and/or external memory, a microcontroller, an embedded microcontroller, a programmable digital signal processor or other programmable devices. In addition, or, as an alternative, the processes may be implemented using an application specific integrated circuit (ASIC), a programmable gate array, a programmable array logic (PAL), or other devices configured to process electronic signals, or combinations thereof. Targets of technical solutions of the present invention or portions contributing to the arts may be configured in a form of program instructions performed by various computer components and stored in non-transitory computer-readable recording media. The media may include, alone or in combination with the program instructions, data files, data structures, and the like. The program instructions recorded in the media may be specially designed and configured for the present invention, or may be known to those skilled in the art of computer software. Examples of the media may include magnetic media such as hard disks, floppy disks, and magnetic tapes; optical media such as CD-ROM discs, DVDs, and Blu-ray; magneto-optical media such as floptical disks; and hardware devices that are specially configured to store and perform program instructions, such as ROM, RAM, flash memory, and the like. Examples of program instructions may include a machine code, such as produced by a compiler and higher language code that may be executed by a computer using an interpreter. Examples of program instructions include both machine code, such as produced by a compiler and files containing structural programming languages such as C++ object-oriented programming language and high or low programming languages (assembly languages, hardware technical languages, database programming languages and techniques) to run not only on one of the aforementioned devices but also a processor, a processor architecture, or a heterogeneous combination of combinations of different hardware and software components, or a machine capable of executing program instructions. Accordingly, they may include a machine language code, a byte code, and a high language code executable using an interpreter and the like.

Therefore, according to aspect of the present disclosure, the aforementioned methods and combinations thereof may be implemented by one or more computing apparatuses as an executable code that performs the respective operations. According to another aspect, the methods may be implemented by systems that perform the operations and may be distributed over a plurality of devices in various manners or all of the functions may be integrated into a single exclusive, stand-alone device, or different hardware. According to still another aspect, devices that perform operations associated with the aforementioned processes may include the aforementioned hardware and/or software. Such all of the sequences and combinations associated with the processes are to be included in the scope of the present disclosure.

For example, the described hardware devices may be to act as one or more software modules in order to perform the operations of the above-described example embodiments, or vice versa. The hardware devices may include a processor, such as, for example, an MPU, a CPU, a GPU, and a TPU, configured to be combined with a memory such as ROM/RAM configured to store program instructions and to execute the instructions stored in the memory, and may include a communicator capable of transmitting and receiving a signal with an external device. In addition, the hardware devices may include a keyboard, a mouse, and an external input device for receiving instructions created by developers.

While the present invention is described with reference to specific matters such as components, some example embodiments, and drawings, they are merely provided to help general understanding of the present invention and this invention is not limited to the example embodiments. It will be apparent to those skilled in the art that various alternations and modifications in forms and details may be made from the present invention.

Therefore, the scope of this disclosure is not defined by the example embodiments, but by the claims and their equivalents, and all variations within the scope of the claims and their equivalents are to be construed as being included in the disclosure.

Such equally or equivalently modified example embodiments may include, for example, logically equivalent methods capable of achieving the same results as those acquired by implementing the method according to this disclosure. Accordingly, the present invention and the scope thereof are not limited to the aforementioned example embodiments and should be understood as a widest meaning allowable by law.

What is claimed is:

1. A method of aiding visualization of lesions in a medical image by a computing apparatus, the method comprising:
generating a first lesion mask for the medical image by inputting the medical image to an artificial neural network;
receiving a first input of a user for modifying the first lesion mask;
determining a selection area based on information about a single point at which the first input of the user is performed; generating a plurality of second lesion masks by inputting the medical image to which the first lesion mask is applied and the selection area to the artificial neural network;

selecting at least one third lesion mask satisfying a specific condition from among the plurality of second lesion masks, wherein the specific condition is determined based on a position of the single point and the selection area;

receiving a second input of the user for selecting a fourth lesion mask from among the at least one third lesion mask by providing the at least one third lesion mask to the user; and determining the fourth lesion mask as a final modified lesion mask.

2. The method of claim 1, wherein the at least one third lesion mask is selected from among the plurality of second lesion masks based on the first lesion mask from which the selection region is excluded, when the single point corresponds to an internal area of the first lesion mask in the medical image, and wherein the at least one third lesion mask is selected from among the plurality of second lesion masks based on a lesion area including the selection area and the first lesion mask, when the single point corresponds to an external area of the first lesion mask in the medical image.

3. The method of claim 1, wherein the selection area is determined as a predetermined shape based on a location of the single point, and wherein a size of the predetermined shape is adjusted or the shape is adjusted based on an additional user input.

4. The method of claim 1, wherein the selection area is determined based on pixel information corresponding to the single point.

5. The method of claim 4, wherein the selection area includes an area of which similarity with the pixel information corresponding to the single point is greater than or equal to a threshold, among areas included in the medical image.

6. The method of claim 1, wherein the first input of the user includes a third input of the for determining a first selection area corresponding to a modified area in the first lesion mask and a fourth input of the user for determining a second selection area corresponding to a non-modified area in the first lesion mask.

7. A non-transitory computer-readable record medium storing a computer program comprising instructions configured to cause a computing apparatus to perform the method of claim 1.

8. A computing apparatus for aiding visualization of lesions in a medical image, the computing apparatus comprising:

a communicator; and a processor, wherein the processor is configured to generate a first lesion mask for the medical image by inputting the medical image to an artificial neural network, receive a first input of a user for modifying the first lesion mask, determine a selection area based on information about a single point at which the first input of the user is performed, generate a plurality of second lesion masks by inputting the medical image to which the first lesion mask is applied and the selection area to the artificial neural network, select at least one third lesion mask satisfying a specific condition from among the plurality of second lesion masks, wherein the specific condition is determined based on a position of the single point and the selection area, receive a second input of the user for selecting a fourth lesion mask from among the at least one third lesion mask by providing the at least one third lesion mask to the user, and determine the fourth lesion mask as a final modified lesion masks.

9. The computing apparatus of claim 8, wherein the at least one third lesion mask is selected from among the plurality of second lesion masks based on the first lesion mask from which the selection region is excluded, when the single point corresponds to an internal area of the first lesion mask in the medical image, and wherein the at least one third lesion mask is selected from among the plurality of second lesion masks based on a lesion area including the selection area and the first lesion mask, when the single point corresponds to an external area of the first lesion mask in the medical image.

* * * * *